US011813444B2

(12) United States Patent
Siess et al.

(10) Patent No.: US 11,813,444 B2
(45) Date of Patent: *Nov. 14, 2023

(54) BLOOD PUMP

(71) Applicant: Abiomed Europe GmbH, Aachen (DE)

(72) Inventors: Thorsten Siess, Aachen (DE); Jimpo Wang, Danvers, MA (US); Gerd Spanier, Aachen (DE)

(73) Assignee: Abiomed Europe GmbH, Aschen (DE)

( * ) Notice: Subject to any disclaimer, the term of this patent is extended or adjusted under 35 U.S.C. 154(b) by 100 days.

This patent is subject to a terminal disclaimer.

(21) Appl. No.: 17/384,111

(22) Filed: Jul. 23, 2021

(65) Prior Publication Data

US 2022/0008713 A1 Jan. 13, 2022

Related U.S. Application Data

(63) Continuation of application No. 16/087,546, filed as application No. PCT/EP2017/056613 on Mar. 21, 2017, now Pat. No. 11,097,092.

(30) Foreign Application Priority Data

Mar. 23, 2016 (EP) ..................................... 16161941

(51) Int. Cl.
*A61M 60/419* (2021.01)
*A61M 60/135* (2021.01)
(Continued)

(52) U.S. Cl.
CPC .......... *A61M 60/419* (2021.01); *A61M 60/13* (2021.01); *A61M 60/139* (2021.01);
(Continued)

(58) Field of Classification Search
CPC .. A61M 60/13; A61M 60/139; A61M 60/216; A61M 60/221; A61M 60/232;
(Continued)

(56) References Cited

U.S. PATENT DOCUMENTS 6,214,541 B1 4/2001 Zentgraf et al.
6,217,541 B1 4/2001 Yu
(Continued)

FOREIGN PATENT DOCUMENTS

CN 101513546 A 8/2009

OTHER PUBLICATIONS

International Search Report (PCT/EP2017/056613) dated Apr. 11, 2017 (4 pages).
(Continued)

*Primary Examiner* — Jon Eric C Morales
(74) *Attorney, Agent, or Firm* — Botos Churchill IP Law LLP

(57) ABSTRACT

An intravascular blood pump comprises a pump casing having a blood flow inlet and a blood flow outlet, and an impeller arranged in said pump casing so as to be rotatable about an axis of rotation, wherein the impeller has blades sized and shaped for conveying blood from the blood flow inlet to the blood flow outlet. The blood pump further comprises a drive unit for rotating the impeller, the drive unit comprising a plurality of posts arranged about the axis of rotation, wherein each of the posts includes a shaft portion and a head portion. Coil windings around the posts are sequentially controllable so as to create a rotating magnetic field. The drive unit further comprises a back plate which engages ends of the shaft portions of the posts opposite the head portions.

27 Claims, 16 Drawing Sheets

(51) Int. Cl.
  *A61M 60/422* (2021.01)
  *A61M 60/824* (2021.01)
  *A61M 60/82* (2021.01)
  *A61M 60/13* (2021.01)
  *A61M 60/139* (2021.01)
  *A61M 60/237* (2021.01)
  *A61M 60/232* (2021.01)
  *A61M 60/216* (2021.01)
  *A61M 60/825* (2021.01)
  *A61M 60/50* (2021.01)

(52) U.S. Cl.
  CPC ........ *A61M 60/216* (2021.01); *A61M 60/232* (2021.01); *A61M 60/237* (2021.01); *A61M 60/422* (2021.01); *A61M 60/50* (2021.01); *A61M 60/82* (2021.01); *A61M 60/824* (2021.01); *A61M 60/825* (2021.01)

(58) Field of Classification Search
  CPC .............. A61M 60/237; A61M 60/419; A61M 60/422; A61M 60/50; A61M 60/82; A61M 60/824; A61M 60/825
  See application file for complete search history.

(56) References Cited

U.S. PATENT DOCUMENTS

| | | |
|---|---|---|
| 11,097,092 B2 * | 8/2021 | Siess ..................... A61M 60/50 |
| 2003/0163019 A1 | 8/2003 | Goldowsky |
| 2011/0238172 A1 | 9/2011 | Akdis |
| 2012/0046514 A1 | 2/2012 | Bourque |
| 2014/0030122 A1 | 1/2014 | Ozaki et al. |
| 2015/0051436 A1 | 2/2015 | Spanier et al. |

OTHER PUBLICATIONS

Office Action from corresponding Chinese Application No. 201780018607.4 dated Feb. 2, 2021 (21 pages).
Extended European Search Report for EP Application No. 23184374.9-112/4241829 dated Sep. 5, 2023 from the EPO.

* cited by examiner

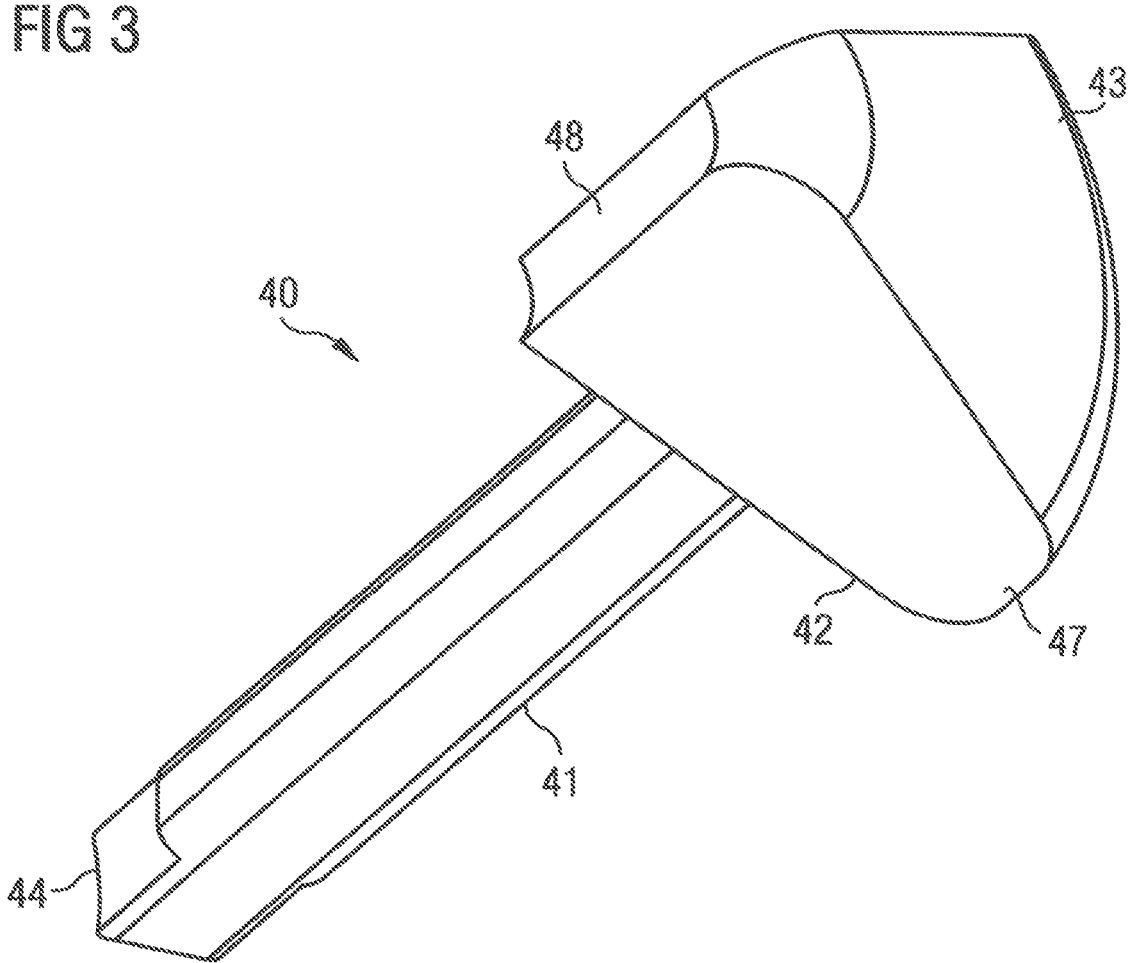

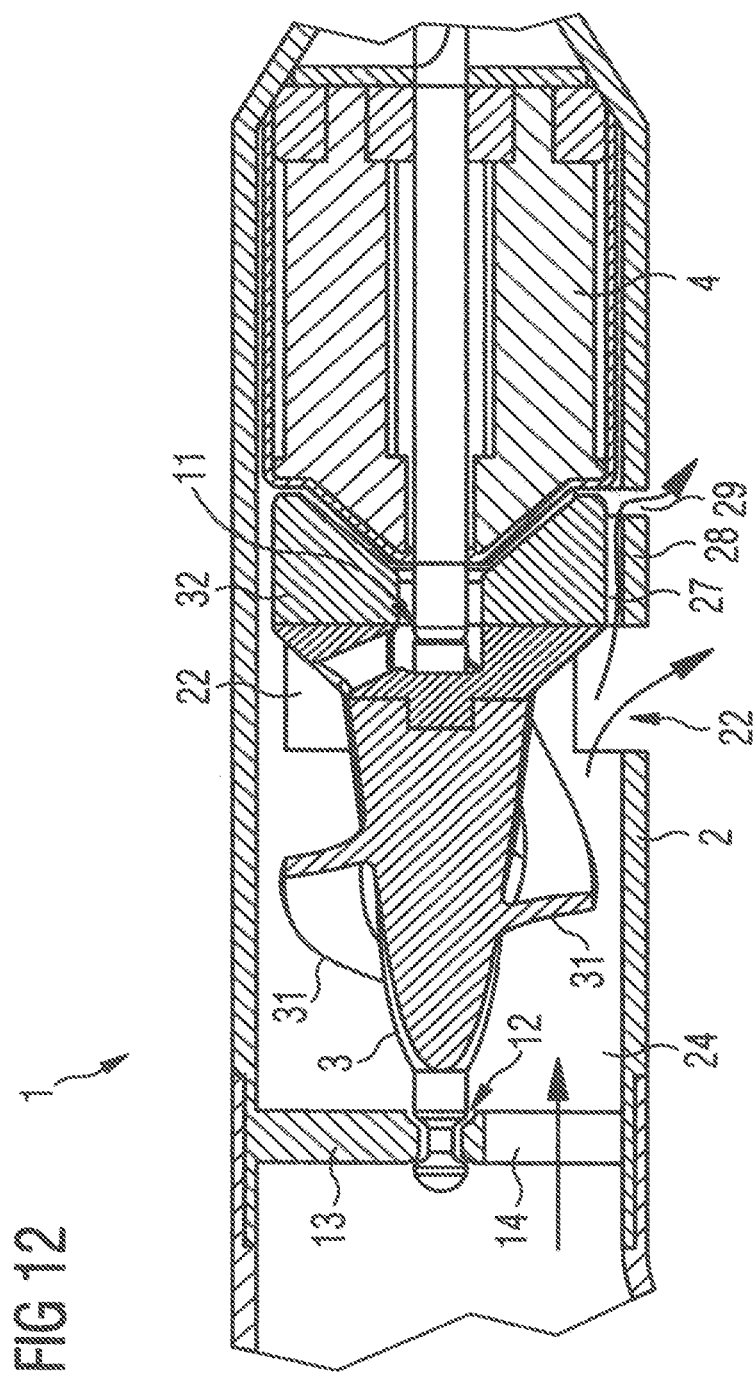

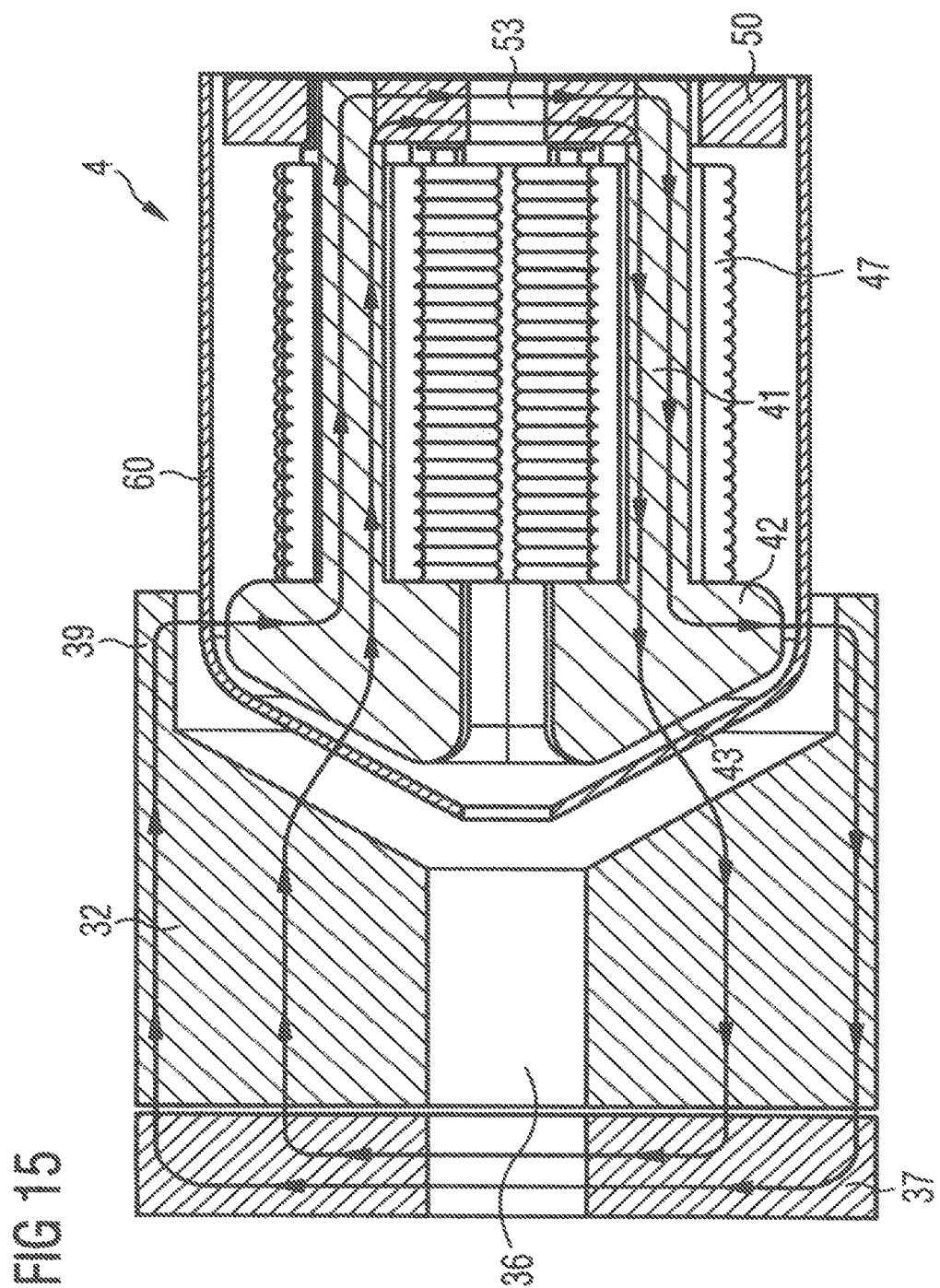

BLOOD PUMP

CROSS-REFERENCE TO RELATED APPLICATIONS

The present application is a continuation of U.S. patent application Ser. No. 16/087,546 (now U.S. Pat. No. 11,097, 092), filed Sep. 21, 2018, which is a national phase entry under 35 U.S.C. § 371 of International Application No. PCT/EP2017/056613, filed Mar. 21, 2017, published as International Publication No. WO 2017/162619 A1, which claims priority from European Patent Application No. 16161941.6, filed on Mar. 23, 2016, the disclosures of which are hereby incorporated herein by reference.

This invention relates to a blood pump, in particular an intravascular blood pump for percutaneous insertion into a patient's blood vessel, to support a blood flow in a patient's blood vessel. The blood pump has an improved drive unit which allows for reduction of the outer diameter of the blood pump.

Blood pumps of different types are known, such as axial blood pumps, centrifugal blood pumps or mixed-type blood pumps, where the blood flow is caused by both axial and radial forces. Intravascular blood pumps are inserted into a patient's vessel such as the aorta by means of a catheter. A blood pump typically comprises a pump casing having a blood flow inlet and a blood flow outlet connected by a passage. In order to cause a blood flow along the passage from the blood flow inlet to the blood flow outlet, an impeller or rotor is rotatably supported within the pump casing, with the impeller being provided with blades for conveying blood.

Blood pumps are typically driven by a drive unit, which can be an electric motor. For instance, US 2011/0238172 A1 discloses extracorporeal blood pumps having an impeller which may be magnetically coupled to an electric motor. The impeller comprises magnets which are disposed adjacent to magnets in the electric motor. Due to attracting forces between the magnets in the impeller and in the motor, rotation of the motor is transmitted to the impeller. In order to reduce the number of rotating parts, it is also known from US 2011/0238172 A1 to utilize a rotating magnetic field, with the drive unit having a plurality of static posts arranged about the axis of rotation, and each post carrying a wire coil winding and acting as a magnetic core. A control unit sequentially supplies a voltage to the coil windings to create the rotating magnetic field. In order to provide a sufficiently strong magnetic coupling, the magnetic forces have to be high enough, which can be achieved by a sufficiently high current supplied to the drive unit or by providing large magnets, which, however, leads to a large overall diameter of the blood pump.

SUMMARY OF THE INVENTION

It is therefore an object of the present invention to provide a blood pump, preferably an intravascular blood pump or transvalvular blood pump, having a magnetic coupling between the drive unit and the impeller, wherein the blood pump has a compact design, in particular a sufficiently small outer diameter to allow the blood pump to be inserted transvascularly, transvenously, transarterially or transvalvularly.

This object is achieved according to the present invention by a blood pump having the features of independent claim 1. Preferred embodiments and further developments of the invention are specified in the claims dependent thereon.

According to the invention, the blood pump, which preferably is an intravascular blood plump and may be one of an axial blood pump, a centrifugal blood pump and a mixed-type blood pump, comprises a drive unit for rotating the impeller. The drive unit comprises a plurality of posts, such as at least two, at least three, at least four, at least five or preferably six posts, that are arranged about the axis of rotation. Higher numbers of posts, such as eight, ten or twelve, may be possible. The number of posts is preferably even for a balanced control of the impeller, but it may also be odd, such as three or five. Each of the posts includes a shaft portion and a head portion, with the head portion pointing towards the impeller. In order to create a rotating magnetic field, a coil winding is disposed about the shaft portion of each of the posts, with the coil windings being sequentially controllable so as to create the rotating magnetic field. The impeller comprises at least one magnet, which is arranged to magnetically couple the impeller to the drive unit, i.e., to interact with the rotating magnetic field so as to cause rotation of the impeller.

A drive unit that creates a rotating electromagnetic field allows for simplification of the mechanics of the blood pump by reducing the number of moving parts compared to a common electric motor. This also reduces wear, because no contact bearing for an electric motor is necessary. The magnetic coupling between the drive unit and the impeller not only causes rotation of the impeller but also permits correct alignment of the impeller. In particular, the magnetic coupling may provide an axial as well as a radial bearing.

In order to increase the density of the magnetic coupling between the drive unit and the magnets of the impeller, it may be advantageous to activate several posts simultaneously, where "activate" means to supply electric power to the respective coil winding in order to create a respective pole magnet. For example, more than half of the posts may be activated at the same time, such as four of six posts, depending on the number of posts and number of magnets in the impeller. Preferably, the arrangement of activated and inactivated posts is rotationally symmetrical and the posts are controlled in pairs.

The drive unit further comprises a back plate which engages ends of the shaft portions of the plurality of posts that are opposite to the head portions. In one embodiment, the back plate may comprise a plurality of apertures arranged about the axis of rotation for receiving said ends of the shaft portions, preferably at a regular angular distance. However, it will be appreciated that the post can be attached, connected or secured to the back plate by other means, either permanently or releasably. The back plate particularly serves for closing the magnetic flux circuit to facilitate and increase the magnetic flux generation and improve the coupling capability. Since the magnetic flux is increased by the back plate, the overall diameter of the blood pump can be reduced, which is particularly advantageous for intravascular blood pumps. The arrangement including the posts with the back plate further allows for high frequencies of the blood pump, i.e., the blood pump can operate at a high speed. In addition, as the back plate engages the posts, the back plate provides structural stability for the post assembly.

The back plate may be made of magnetic steel or other material suitable for closing the magnetic flux circuit, preferably cobalt steel. The diameter of the back plate may be about 3 mm to 9 mm, such as 5 mm or 6 mm to 7 mm. The thickness of the back plate may be about 0.5 mm to about 2.5 mm, such as 1.5 mm. The outer diameter of the blood pump may be from about 4 mm to about 10 mm, preferably about 6 mm. The outer diameter of the arrangement of the plurality of posts, in particular the largest outer diameter of the arrangement of the plurality of posts which is measured at the head portions of the posts may be about 3 mm to 8 mm, such as 4 mm to 6 mm, preferably 5 mm.

The dimensions of the posts, in particular length and cross-sectional area, may vary and depend on various factors. In contrast to the dimensions of the blood pump, e.g., the outer diameter, which depend on the application of the blood pump, the dimensions of the posts are determined by electromagnetic properties, which are adjusted to achieve a desired performance of the drive unit. One of the factors is the flux density to be achieved through the smallest cross-sectional area of the posts. The smaller the cross-sectional area, the higher is the necessary current to achieve the desired magnetic flux. A higher current, however, generates more heat in the wire of the coil due to electrical resistance. That means, although "thin" posts are preferred to reduce the overall size, this would require high current and, thus, result in undesired heat. The heat generated in the wire also depends on the length and diameter of the wire used for the coil windings. A short wire length and a large wire diameter are preferred in order to minimize the winding loss (referred to as "copper loss" or "copper power loss" if copper wires are used, which is usually the case). In other words, if the wire diameter is small, more heat is generated compared to a thicker wire at the same current, a preferred wire diameter being e.g., 0.05 mm to 0.2 mm, such as 0.1 mm. Further factors influencing the post dimensions and the performance of the drive unit are the number of windings of the coil and the outer diameter of the windings, i.e., the post including the windings. A large number of windings may be arranged in more than one layer around each post, for instance, two or three layers may be provided. However, the higher the number of layers, the more heat will be generated due to the increased length of the wire in the outer layers having a larger winding diameter. The increased length of the wire may generate more heat due to the higher resistance of a long wire compared to a shorter one. Thus, a single layer of windings with a small winding diameter would be preferred.

A typical number of windings, which in turn depends on the length of the post, may be about 50 to about 150, e.g., 56 or 132.

In one embodiment, the impeller may also comprise a yoke or back plate that is attached to the at least one magnet of the impeller, preferably at a side of the impeller facing away from the drive unit, e.g., between the magnet and blades of the impeller. Like the back plate that is attached to the ends of the shafts of the posts, the yoke or back plate of the impeller serves for closing the magnetic flux circuit to increase the magnetic flux generation and enhance the coupling capability. It may be made of magnetic steel, preferably cobalt steel.

The posts may be made of magnetic steel, too. Preferably, the drive unit, including the posts and the back plate, is made of cobalt steel. The use of the cobalt steel contributes to reducing the pump size, in particular the diameter. With the highest magnetic permeability and highest magnetic saturation flux density among all magnetic steels, cobalt steel produces the most magnetic flux for the same amount of material used.

It may be further advantageous for the efficiency and performance of the drive unit if the posts are magnetically insulated against each other. Thus, a magnetically insulating material may be disposed between the head portions of adjacent posts so as to separate the posts from each other and keep the respective magnetic field within the respective post. The magnetically insulating material may be a magnetic material, the magnetic field of which keeps the electromagnetic field caused by the coil windings within the respective post. At least, an air gap or other insulating, i.e., electrically non-conductive, material may be provided between the head portions of the posts to avoid a short-circuit between the posts.

In one embodiment, the head portion of at least one of the posts, preferably of each of the posts, has a top surface that is inclined at an angle relative to a plane perpendicular to the axis of rotation. A distance between the axis of rotation and a center in a radial direction of said inclined surface may be less than or equal to a distance between the axis of rotation and a center in a radial direction of a cross-sectional area of the shaft portion of the respective post. The center in a radial direction of a surface or area is the center between a radially innermost point and a radially outermost point of the surface or area. In other words, the inclined top surface of the head portion, which is the surface facing the impeller, may extend obliquely or may be inclined at an angle relative to the axis of rotation, and half or more of the inclined surface may be located radially inwards relative to the center of the shaft portion. This enables the outer diameter of the drive unit and, thus, of the blood pump, to be kept at a minimum that is necessary for magnetically coupling the drive unit to the impeller. This reduced diameter design is particularly advantageous for intravascular blood pumps that are located within a patient's blood vessel during pump operation and can be deployed by means of a catheter. In addition, the inclined coupling surface provides for radial centering of the impeller. The aforementioned angle is preferably 45°, but may be between about 0° and about 90°, preferably between about 30° and about 60°, more preferably between about 40° to about 50°, with respect to a plane perpendicular to the axis of rotation. The inclined surfaces of the posts preferably face radially outwards, i.e., they form a convex shape. Alternatively, the inclined surfaces may face radially inwards to form a concave shape.

All of the posts preferably are identical such that the drive unit is symmetrical with respect to the axis of rotation. It will be appreciated, however, that the posts do not have to be exactly identical as long as they are compatible for forming the drive unit according to the invention. However, it is preferable for shaft portions to have the same length and the inclined surfaces of the head portions to have the same angle of inclination. Different posts may be irregularly or regularly arranged to form the drive unit, such as in an alternating manner.

The inclined surface of the head portion of said at least one post, preferably of each of the head portions, may be radially aligned with or be located radially inwards or outwards with respect to a radially outermost surface of the coil winding of the respective post. The inclined surface preferably extends radially inwards beyond the respective shaft portion towards the axis of rotation so as to maximize the surface area of the magnetic bearing, while minimizing the outer diameter of the drive unit. For instance, in an axial projection, i.e., as seen in a top view in an axial direction, the inclined surface of the head portion may be located within the coil winding or may be at least aligned with the shaft or coil winding in an axial direction. In another embodiment, the head portion may extend beyond the outer circumference of the coil winding in a radial and/or circumferential direction. The head portion may have a larger cross-sectional dimension than the respective shaft portion in a plane perpendicular to the axis of rotation, with the respective coil winding preferably not extending beyond the head portion at least in a radial direction. In other words, the head portion may form a shoulder, which can act as an axial stop for the coil winding as well as a radial limitation.

At least one of the head portions, preferably all head portions, may be substantially triangular or trapezoidal in cross-section along a plane including the axis of rotation. In the assembled state, the oblique or inclined surfaces of the head portions may together form a conical surface or substantially conical surface, e.g., a surface having facets but forming approximately a conical surface. Generally, the shape of the formed surface can be convex. Illustratively speaking, the head portions may be put together like pie slices to form a circular arrangement having a conical top surface. The at least one magnet of the impeller may have or may form a conical or substantially conical recess substantially corresponding in size and shape to the conical surface formed by the head portions of the posts. Generally, the magnet may form a concave surface facing the convex surface formed by the posts to improve the magnetic coupling. In another embodiment, the arrangement of concave and convex surfaces may be vice versa, i.e., the head portions of the posts may form a conical recess while the magnet forms a convex conical surface.

The respective convex and concave surfaces of the drive unit and the impeller respectively may form a gap such that the distance between the surfaces is constant. Preferably, however, the gap distance is not constant but is chosen such that the cross-sectional area of the gap, viewed in a circumferential direction, is constant in a radial direction. In the latter case the distance between the surfaces increases towards the axis of rotation. Combinations may also be envisioned. The shape and dimension of the gap between the impeller and the drive unit may contribute to hydrodynamic bearing capabilities.

The magnet of the impeller may be formed as a single piece having the conical or substantially conical recess that corresponds to the shape of the head portions of the posts, including a gap with varying distance as explained above. It will be appreciated, however, that there may be provided a plurality of magnets, such as two or more, e.g., four, preferably six magnets, or even eight, ten or twelve magnets, that are arranged in the impeller about the axis of rotation and form the conical recess. Providing a plurality of magnets, preferably an even number, more preferably a number corresponding to the number of posts, is advantageous because the magnets can be arranged with alternating north/south orientations of the magnetic field without dead zones. If the magnet is provided as a single piece, dead zones may be created at the transitions between differently oriented magnetic fields.

If the impeller includes a plurality of magnets, the magnets may be arranged with substantially no gaps between the individual magnets in order to increase the amount of magnetic material. However, it has been found that the efficiency of the magnetic coupling does not decrease if the magnets are separated by gaps, in particular radially extending gaps. This is because of the characteristics of the magnetic field and the gap between the drive unit and the impeller. If the magnets in the impeller are close to each other, the innermost magnetic field lines, which extend in an arch from one magnet (north) to an adjacent magnet (south), do not extend beyond the gap between the drive unit and the impeller and, thus, do not reach the drive unit, i.e., they do not contribute to the drive of the impeller. Therefore, there is no loss in efficiency if a gap is provided between the magnets in the impeller. The size of gap between the magnets in the impeller that can be provided without loss of efficiency of the drive is dependent on the size of the gap between the impeller and the drive unit as a skilled person can calculate. The gaps between the impeller magnets can then be used e.g., as wash out channels.

Generally speaking, and regardless of whether the head portions form a conical surface, the magnet of the impeller may have a surface that faces the head portions of the posts and is inclined at an angle substantially corresponding to the angle of the inclined surfaces of the head portions. For instance, the arrangement may be the converse of the aforementioned arrangement, that is to say, the head portions of the posts may form a concave surface, such as a conical recess, and the magnet of the impeller may form a convex surface, such as a conical surface.

Regardless of the inclination of the respective surfaces, the magnet or magnets of the impeller may be radially aligned with the head portions of the posts. However, in some embodiments, the magnet or magnets of the impeller may be radially offset with respect to the head portions of the posts, such as radially inwards or radially outwards. This radial offset may improve stabilizing and radial centering of the impeller because the magnetic forces between the impeller and the drive unit have a radial component, whereas the magnetic forces are directed merely substantially axially if the magnets are radially aligned with the head portion of the posts.

In one embodiment, the impeller may extend at least partially about the drive unit, in particular the head portions of the posts. In other words, the impeller may have an extension that overlaps the drive unit in a circumferential direction. That means the magnetic coupling takes place not only in the region of the inclined surfaces of the head portions of the posts but also on radially outer side surfaces thereof. The impeller may have an increased diameter, in particular a larger diameter than the drive unit, such that the impeller can extend about the area of the head portions of the posts. The impeller may, thus, have a recess that has a conical portion as described above and a cylindrical portion. The magnetic coupling can be improved by this design of the impeller because the impeller and the drive unit are coupled in a radial direction as well, where the magnetic field lines extend in a radial direction. In this area a high torque can be created to drive the impeller due to the largest diameter.

In one embodiment, the intravascular blood pump may further comprise a housing surrounding the drive unit, with the housing preferably corresponding in size and shape to an outer contour of the plurality of posts. In particular, the housing may have a conical axial end surface corresponding to the shape of the surface formed by the inclined surfaces of the posts' head portions. The opposite end may be open and may engage the back plate to close the housing. The housing serves as a protection for the post assembly, particularly as a protection against blood contact, which is particularly useful for the coil windings. Preferably, the housing is disposed inside the pump casing. Regardless of the presence of such housing, the drive unit preferably is arranged inside the pump casing. The housing is preferably made of a non-magnetic and non-conductive (i.e., electrically insulating) material and provides good heat transfer. The material of the housing may be e.g., aluminum.

The coil windings may be embedded in a thermally conductive matrix, which is electrically non-conductive (i.e., electrically insulating). The matrix protects the coil windings and transfers heat produced by the coil windings. The material of the thermally conductive matrix maybe a plastics material with additives in order to increase the thermally conductive characteristics. For instance, the matrix may comprise an epoxy resin with aluminum additives. The matrix may be formed by molding the material around and between the coil windings and subsequently curing the material.

Preferably, the drive unit has a central opening that extends along the axis of rotation. The central opening may be formed by the head portions of the posts and may be configured for receiving an elongate pin, with an axial end surface of the pin being sized and dimensioned to form a bearing surface for the impeller. This arrangement allows for a compact design of the blood pump because the space between the posts is used for the pin. The other end of the pin may be supported by the pump casing. The central opening may also be provided for insertion of a guide wire or the like or may form a fluid path.

In order to enhance a wash-out flow through the gap between the impeller and the drive unit, a secondary set of blades may be provided in the impeller. In particular, secondary blades may be provided on the side of the magnet or magnets that faces the drive unit, i.e., in the gap between the impeller and the drive unit. The wash-out flow may additionally or alternatively be increased by channels that are recessed in the surface of the magnet that faces the drive unit. The channels may extend e.g., radially or helically.

In one embodiment, one or more hydrodynamic bearings may be provided to support the impeller. For instance, the aforementioned secondary blades and the channels may form a hydrodynamic bearing or at least support hydrodynamic bearing capabilities as mentioned above with respect to the size and shape of the gap between the impeller and the drive unit. Conversely, the surface of the drive unit that faces the impeller, i.e., in particular the end surface of the housing that encloses the drive unit, may be adapted to form a hydrodynamic bearing. The hydrodynamic bearing may be axial or radial or both axial and radial. In particular because of the conical shape of the interface between the impeller and the drive unit, a hydrodynamic bearing in both radial and axial directions can be formed. A radial hydrodynamic bearing may also be formed between an outer surface of the impeller and an inner surface of the pump casing. In particular, a gap may be formed between the impeller and the pump casing, where an amount of blood sufficient for the hydrodynamic bearing flows through the gap and exits the pump casing through an additional blood flow outlet. The main blood flow exits the pump casing through the blood flow outlet and does not flow through the gap. Hydrodynamic bearings, which are contactless bearings, may support the function of the drive unit by reducing frictional forces.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings:

FIG. 3 shows a perspective view of a post of a drive unit.

FIG. 4a shows a cross-sectional view of the post along line A-A in FIG. 4d, FIG. 4b shows a side view of the post, FIG. 4c shows a bottom view of the post, and FIG. 4d shows a top view of the post.

FIG. 9a shows a top view of the back plate, FIG. 9b shows a cross-sectional view of the back plate along line A-A in FIG. 9a, and FIG. 9c shows a cross-sectional view of the back plate along line B-B in FIG. 9a.

FIG. 10a shows a top view of the magnets, FIG. 10b shows a side cross-sectional view of the magnets along line A-A in FIG. 10a, and FIG. 10c shows a perspective view of the magnets.

FIG. 12 shows another embodiment of a blood pump.

FIG. 15 shows a cross-sectional view of a drive unit and impeller magnets according to another embodiment.

DETAILED DESCRIPTION

Figure 1:
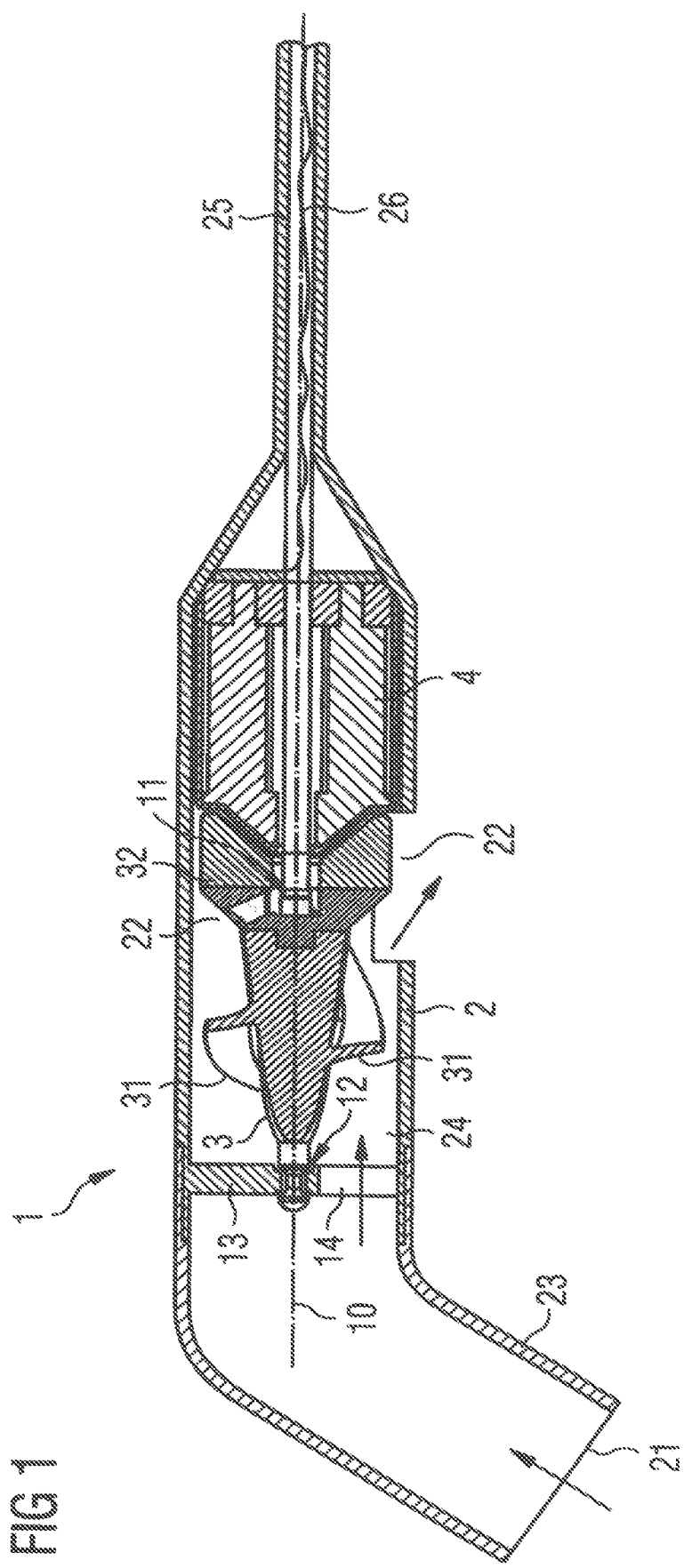
FIG. 1 shows a cross-sectional view of a blood pump according to the invention.
Figure 2:
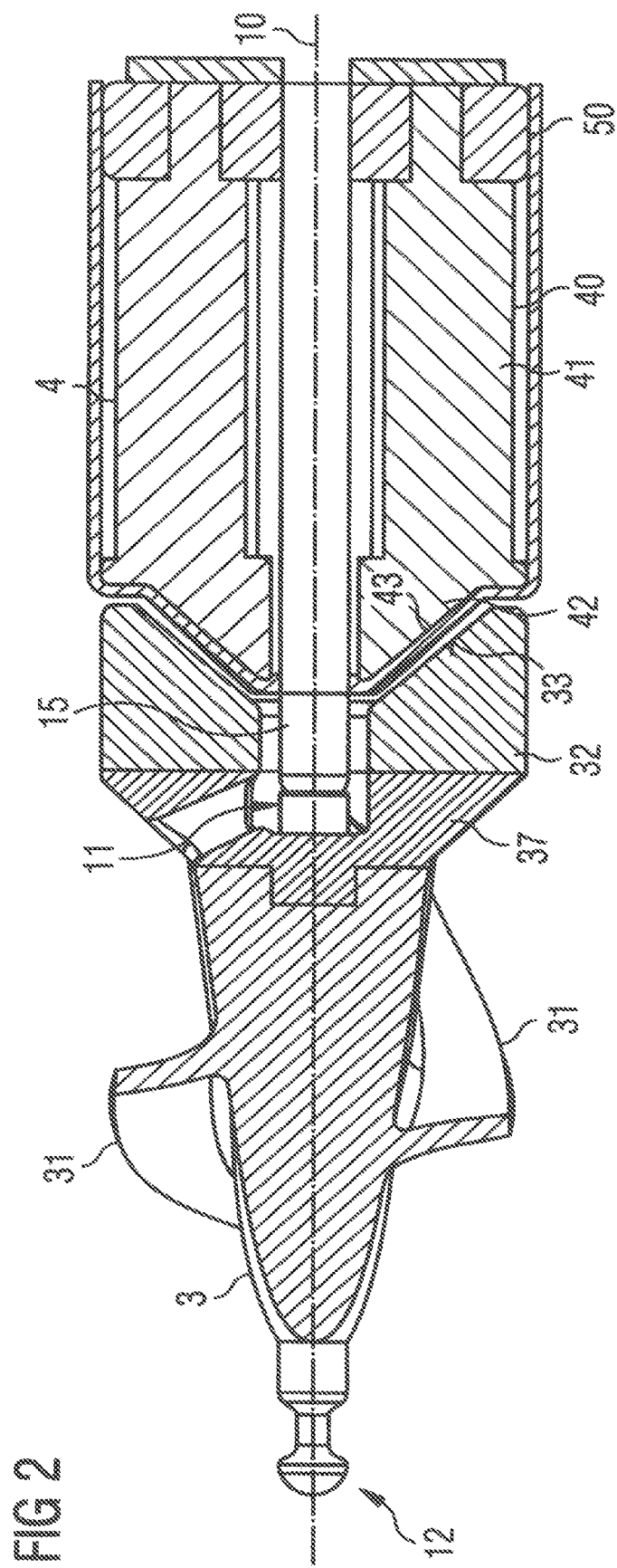
FIG. 2 shows an enlarged detail of the blood pump of FIG. 1.
Figure 4A:
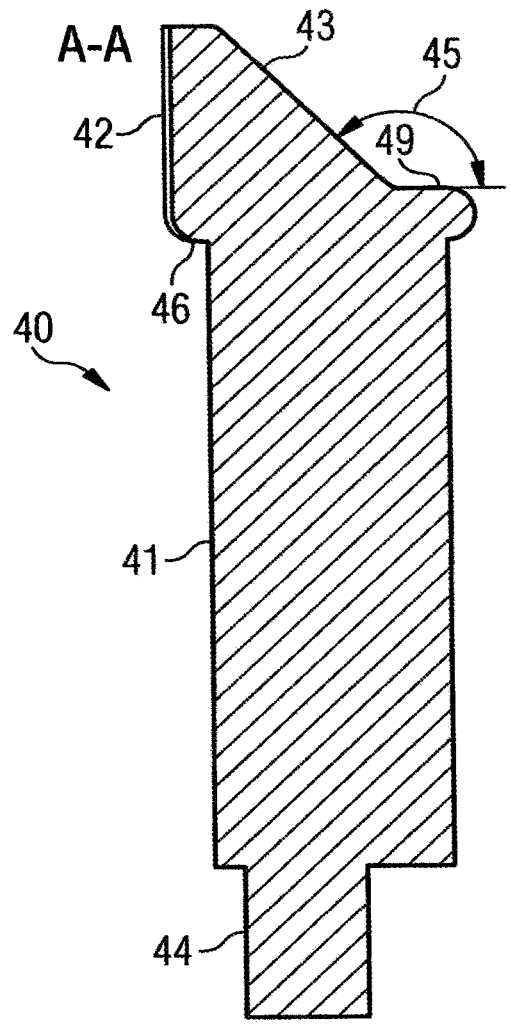
FIGS. 4a-4d show different views of another embodiment of a post, where
Figure 4B:
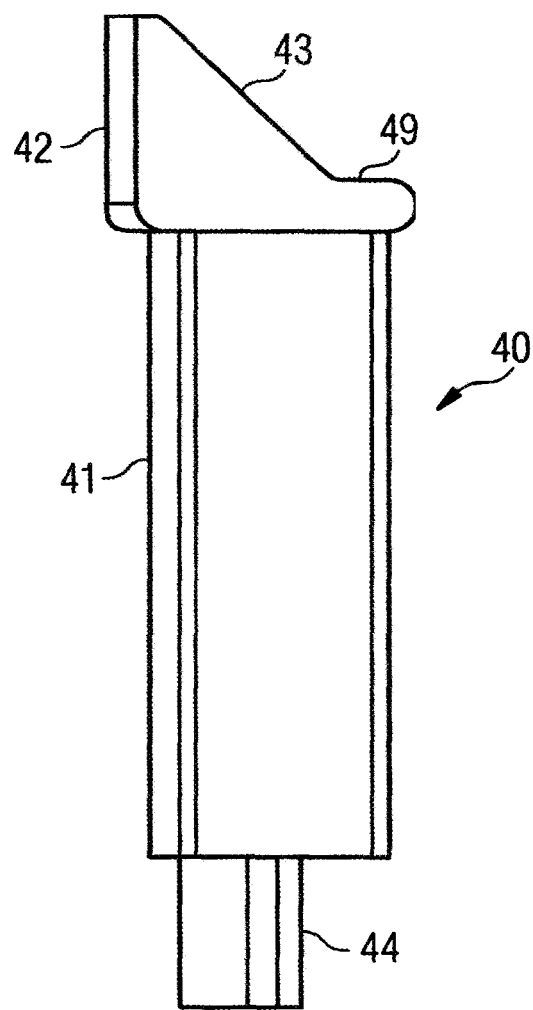
Figure 4C:
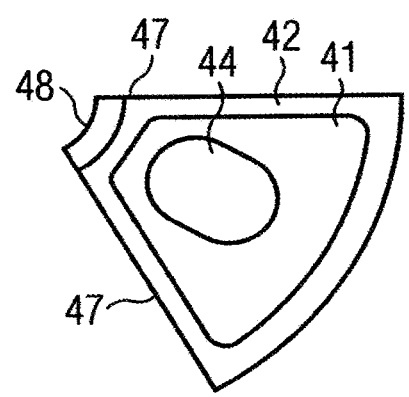
Figure 4D:
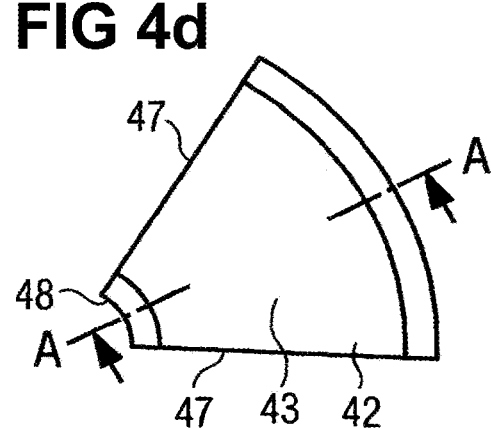

Referring to FIG. 1, a cross-sectional view of a blood pump 1 is illustrated. FIG. 2 shows an enlarged view of the interior of the blood pump 1. The blood pump 1 comprises a pump casing 2 with a blood flow inlet 21 and a blood flow outlet 22. The blood pump 1 is designed as an intravascular pump, also called a catheter pump, and is deployed into a patient's blood vessel by means of a catheter 25. The blood flow inlet 21 is at the end of a flexible cannula 23 which may be placed through a heart valve, such as the aortic valve, during use. The blood flow outlet 22 is located in a side surface of the pump casing 2 and may be placed in a heart vessel, such as the aorta. The blood pump 1 is connected to the catheter 25, with an electric line 26 extending through the catheter 25 for supplying the blood pump 1 with electric power in order to drive the pump 1 by means of a drive unit 4, as explained in more detail below.

The blood is conveyed along a passage 24 connecting the blood flow inlet 21 and the blood flow outlet 22 (blood flow indicated by arrows). An impeller 3 is provided for conveying blood along the passage 24 and is mounted to be rotatable about an axis of rotation 10 within the pump casing 2 by means of a first bearing 11 and a second bearing 12. The axis of rotation 10 is preferably the longitudinal axis of the impeller 3. Both bearings 11, 12 are contact-type bearings in this embodiment. At least one of the bearings 11, 12 could be a non-contact-type bearing, however, such as a magnetic or hydrodynamic bearing. The first bearing 11 is a pivot bearing having spherical bearing surfaces that allow for rotational movement as well as pivoting movement to some degree. A pin 15 is provided, forming one of the bearing surfaces. The second bearing 12 is disposed in a supporting member 13 to stabilize the rotation of the impeller 3, the supporting member 13 having at least one opening 14 for the blood flow. Blades 31 are provided on the impeller 3 for conveying blood once the impeller 3 rotates. Rotation of the impeller 3 is caused by a drive unit 4 magnetically coupled to a magnet 32 at an end portion of the impeller 3. The illustrated blood pump 1 is a mixed-type blood pump, with the major direction of flow being axial. It will be appreciated that the blood pump 1 could also be a purely axial blood pump, depending on the arrangement of the impeller 3, in particular the blades 31.

FIG. 2 illustrates in more detail the interior of the blood pump 1, in particular the impeller 3 and the drive unit 4. The drive unit 4 comprises a plurality of posts 40, such as six posts 40, only two of which are visible in the cross-sectional view of FIG. 2. The posts 40 have a shaft portion 41 and a head portion 42. The head portion 42 is disposed adjacent to the impeller 3 in order to magnetically couple the drive unit 4 to the impeller 3. For this purpose, the impeller 3 has a magnet 32, which is formed as a multiple piece magnet in this embodiment as described in more detail with reference to FIGS. 10a-c. The magnet 32 is disposed at the end of the impeller 3 facing the drive unit 4. The posts 40 are sequentially controlled by a control unit (not shown) in order to create a rotating magnetic field for driving the blood pump 1. The magnet 32 is arranged to interact with the rotating magnetic field so as to cause rotation of the impeller 3 about the axis of rotation 10. Coil windings are arranged about the shaft portions 41 of the posts 40, as described in more detail below with reference to FIG. 7.

In order to close the magnetic flux path, a back plate 50 is located at the end of the shaft portions 41 opposite the head portions 42. The posts 40 act as a magnetic core and are made of a suitable material, such as steel or a suitable alloy, in particular cobalt steel. Likewise, the back plate 50 is made of a suitable magnetic material, such as cobalt steel. The back plate 50 enhances the magnetic flux, which allows for reduction of the overall diameter of the blood pump 1, which is important for intravascular blood pumps. For the same purpose, a yoke 37, i.e., an additional back plate, is provided in the impeller 3 at a side of the magnet 32 facing away from the drive unit 4. The yoke 37 in this embodiment has a conical shape in order to guide the blood flow along the impeller 3. The yoke 37 may be made of cobalt steel, too. One or more wash-out channels that extend towards the central bearing may be formed in the yoke 37 or the magnet 32.

Details of the drive unit 4 are shown in FIGS. 3 to 9, while FIG. 10 illustrates the magnet 32 of the impeller 3. Referring to FIG. 3, one of the posts 40 is shown in a perspective view. In this embodiment, all of the posts 40 in the assembly (i.e., six posts 40) are identical. The post 40 includes a shaft portion 41 and a head portion 42. The head portion 42 has an inclined surface 43, angled at 60° with respect to the longitudinal axis in this embodiment (i.e., 30° with respect to a plane perpendicular to the longitudinal axis). The shaft portion 41 includes an end portion 44 opposite the head portion 42, having a reduced diameter for engaging the back plate 50. The head portion 42 has a larger cross-sectional dimension than the shaft portion 41 in a plane perpendicular to the longitudinal axis. The head portion 42 has side surfaces 47 that are adjacent to the side surfaces of an adjacent post when assembled to form the drive unit 4. In order to avoid a short-circuit of the magnetic flux between the posts 40, a small air gap or other type of insulation is provided between the head portions 42. Further to avoiding a short-circuit, it may be advantageous to provide an insulation material between the head portions 42 of the posts 40 that keeps the magnetic field within each of the posts 40. In other words, the head portions 42 may be separated by a magnetically insulating material. For instance, magnets, e.g., plates of a magnetic material, can be arranged between the head portions 42 to separate the head portions 42 and the respective magnetic fields from each other. Radially inner surfaces 48 of the post head portions 42 form a central opening 54. It will be appreciated that the transition surface between the surfaces 43 and 48 does not need to be rounded.

Different views of another embodiment of a post 40 are shown in FIG. 4, which corresponds to the previous embodiment except for slight changes in the shape of the shaft portion 41 and the head portion 42. FIG. 4a shows a cross-sectional view along the line A-A illustrated in FIG. 4d, which shows a top view (i.e., towards the head portion 42) of the post 40. FIG. 4b shows a perspective view of the post 40, while FIG. 4c shows a bottom view (i.e., a view towards the end portion 44 of the shaft portion 41). The post 40 may have an overall length of about 9 to 10 mm, wherein the head portion 42 may have a length of about 2 mm. In this embodiment, the head portion 42 has a surface 43 which is inclined at an angle of 45° with respect to the axis of rotation or longitudinal axis. Accordingly, the angle 45 between the surface 43 and a ledge 49 shown in FIG. 4a is 135°. The ledge 49 may serve as a stop when the posts 40 are assembled in a housing. Furthermore, a shoulder 46 is formed by the head portion 42, which may serve as a stop for a coil winding. As described in connection with FIG. 3, the head portion 42 comprises side surfaces 47 and a radial inner surface 48.

Figure 5:
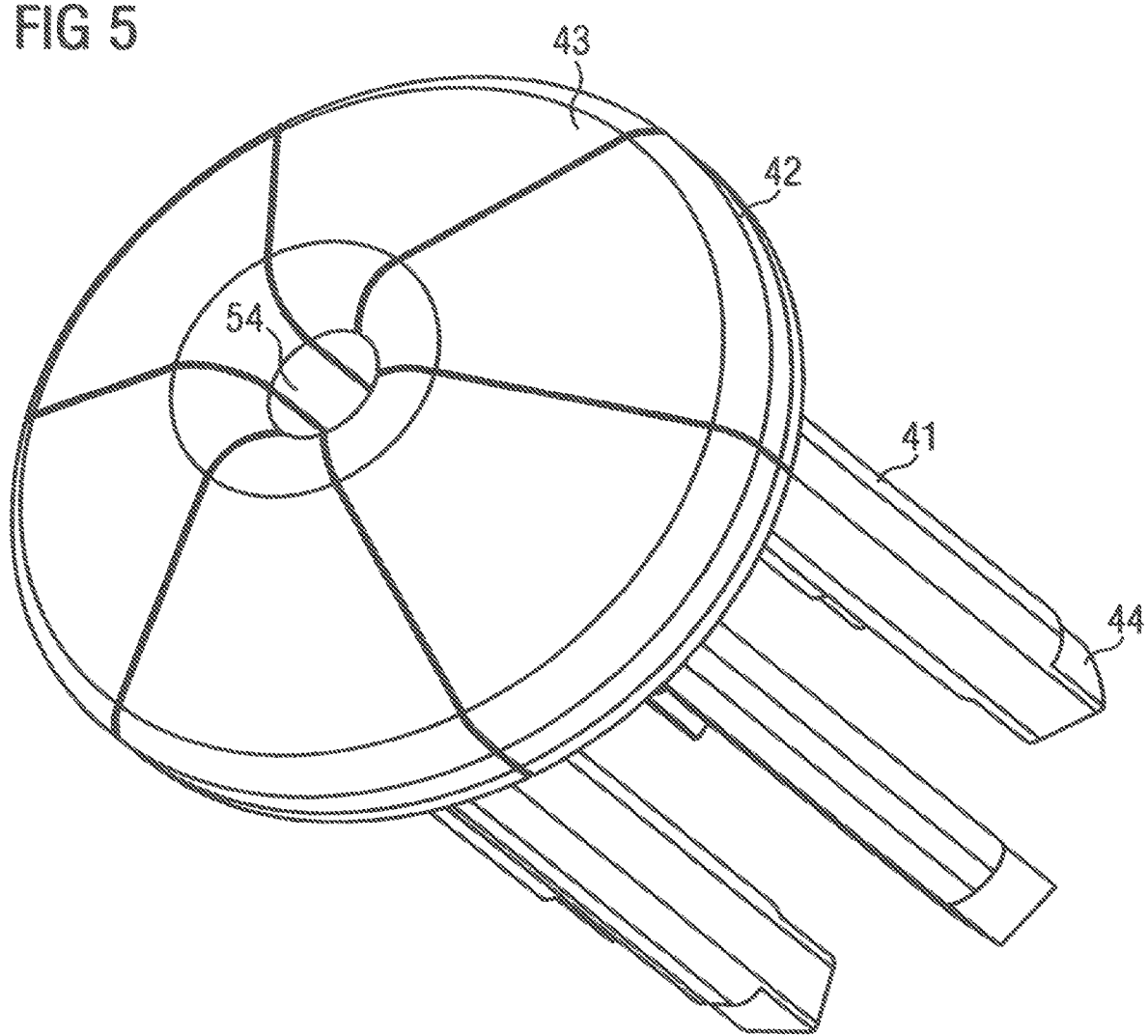
FIG. 5 shows an arrangement including six posts.
Figure 6:
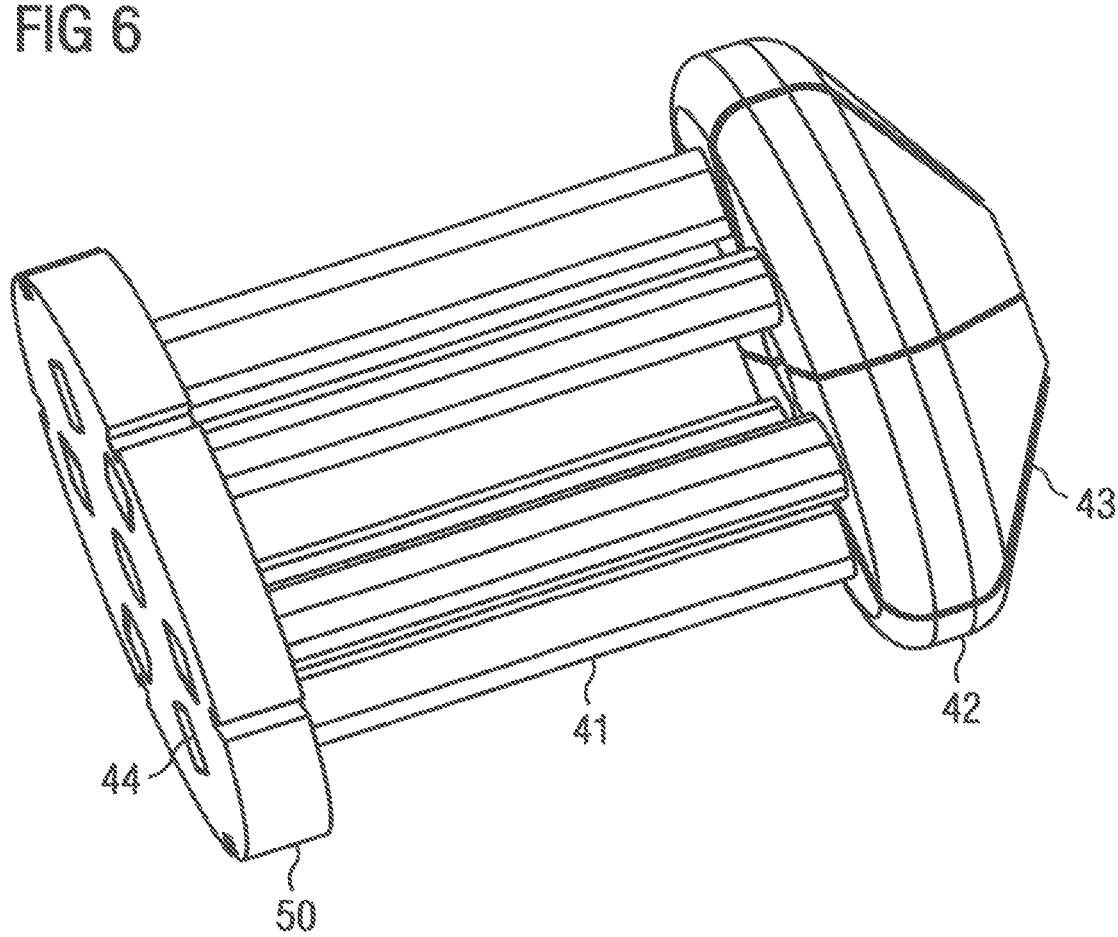
FIG. 6 shows the arrangement of FIG. 5 along with a back plate.

FIG. 5 illustrates an assembly including six posts 40, described in connection with FIG. 3. All posts 40 are formed identically, such that each head portion 42 forms a 60° segment of a circle, that is to say, a "pie slice" of 60°. It will be appreciated that the assembly may include fewer or more posts, such as two, three, four or five or more than six, where the angle depends on the number of posts, e.g., four posts that each form a 90° segment or eight posts that each form a 45° segment. As already mentioned above, the number of posts 40 is preferably even, where diametrically opposed posts 40 may form a pair, e.g., with respect to control of the magnetic field, i.e., each pair of posts may be controlled as a unit to activate the posts of each respective pair simultaneously. The head portions 42 form a cone having a conical surface formed by the inclined surfaces 43. This can be seen more clearly in FIG. 6. In FIG. 6, the reduced-diameter end portions 44 of the shaft portions 41 are mounted in the back plate 50.

Figure 7:
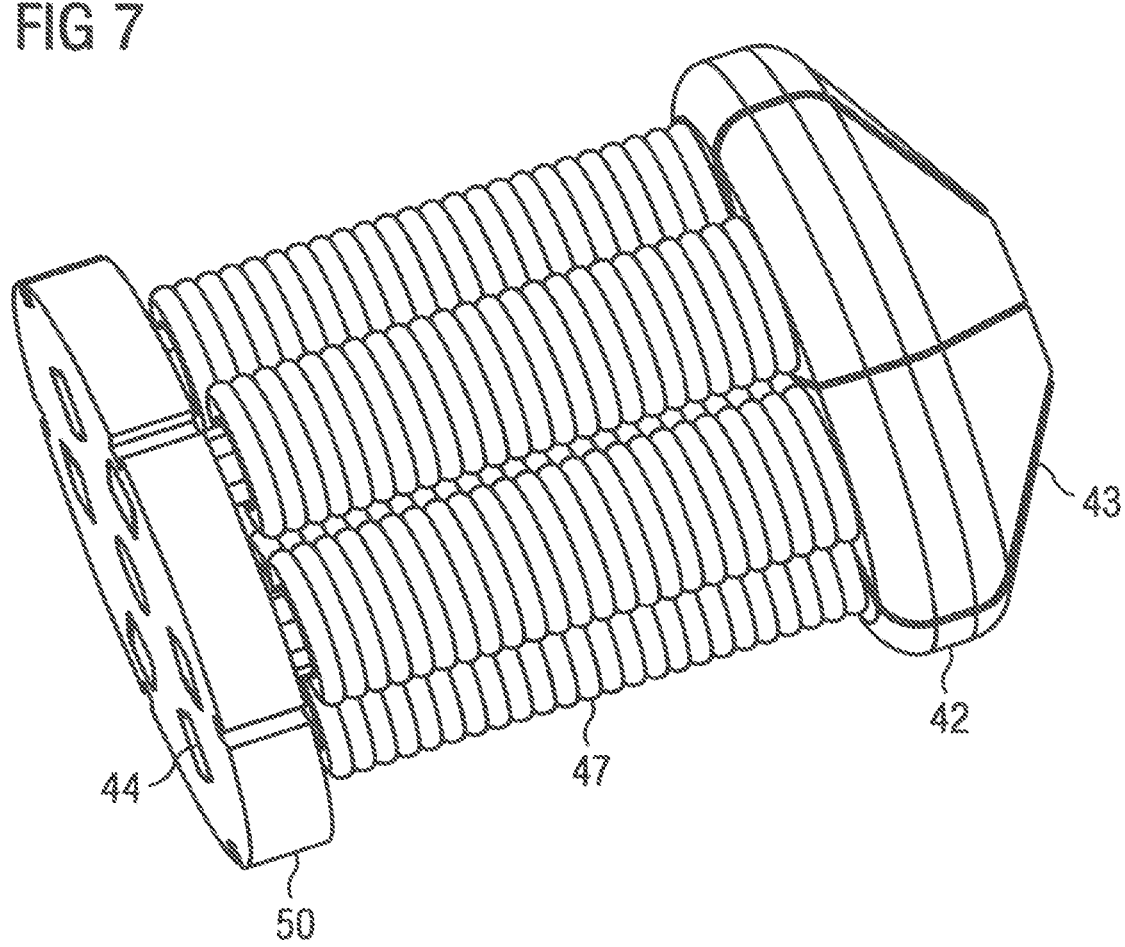
FIG. 7 shows the arrangement of FIG. 6 along with coil windings.
Figure 8:
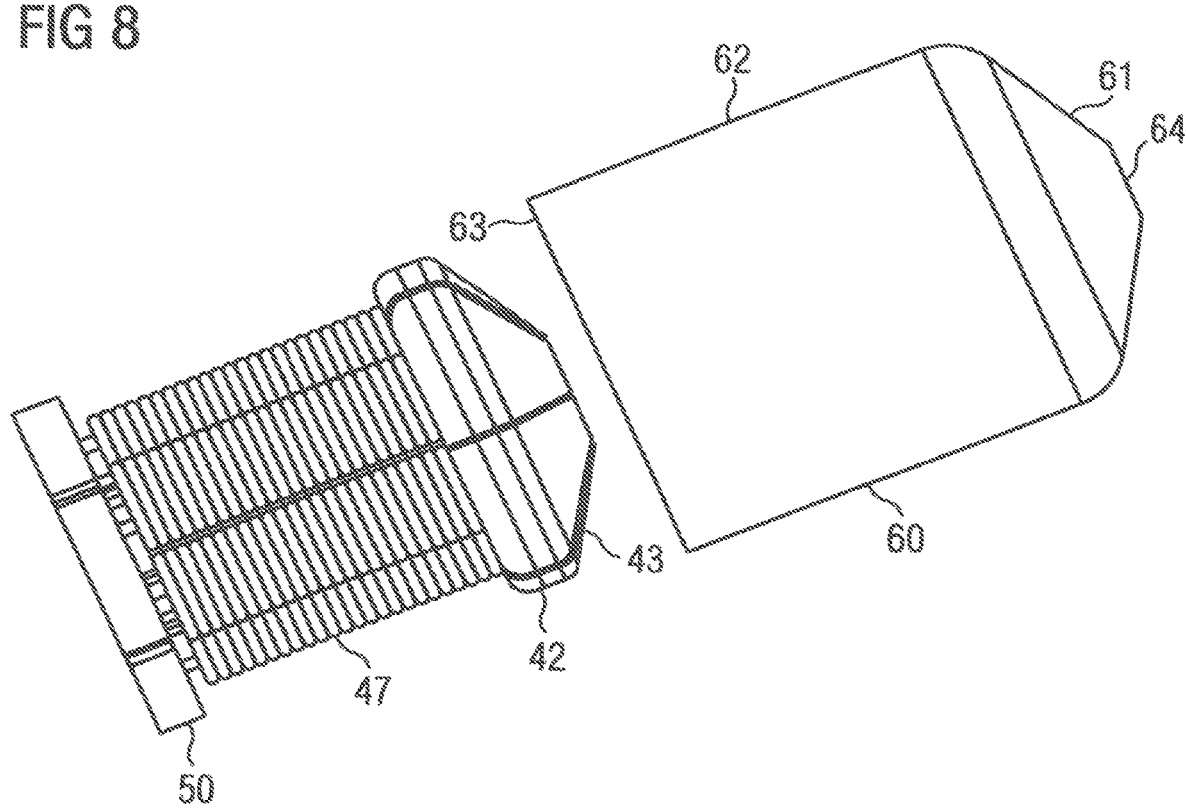
FIG. 8 shows the arrangement of FIG. 7 along with a housing.

In FIG. 7 the same arrangement is illustrated including coil windings 47 about the posts 40. The coil windings 47 do not extend radially beyond the head portions 42, thereby providing for a compact outer dimension. It will be appreciated that preferably the maximum cross-sectional area defined by the head portions 42 is used for the coil windings 47 to optimize usage of the available space and to minimize air gaps that act as an insulator and affect the magnetic flux. Further, the diameter of the shaft portions 41 of the posts 40 is chosen so as to optimize the number of windings of the coil windings 47. FIG. 8 shows a housing 60 which is to be mounted over the post arrangement. The housing 60 conforms to the shape of the post arrangement and comprises a substantially cylindrical portion 62 and a conical end portion 61. The conical end portion 61 is tapered at the same angle as the conical surface formed by the inclined surfaces 43 of the posts' head portions 42, that is to say, the angle preferably is between about 30° to 60°, preferably 30° or 45°, with respect to a plane perpendicular to the longitudinal axis. The housing 60 is closed by the back plate 50 at an open end 63 opposite the conical end portion 61. The conical end portion 61 has a central opening 64 that is aligned with the central opening 54 formed by the posts 40 and a central opening 53 in the back plate 50.

Figure 9A:
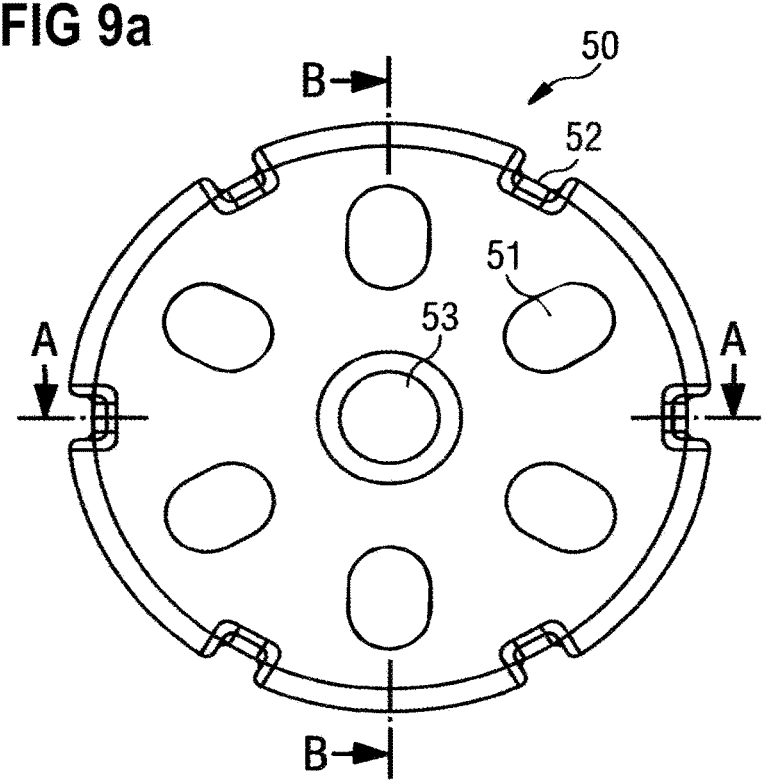
FIGS. 9a-9c show different views of a back plate, where
Figure 9C:
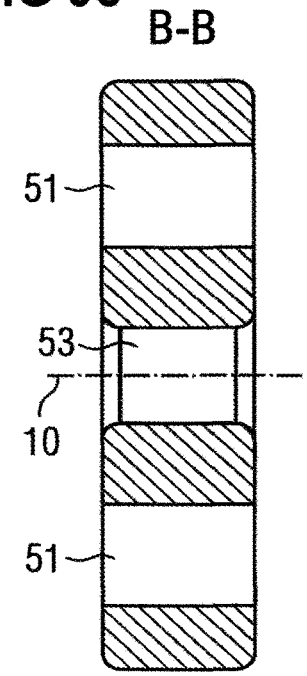
Figure 9B:
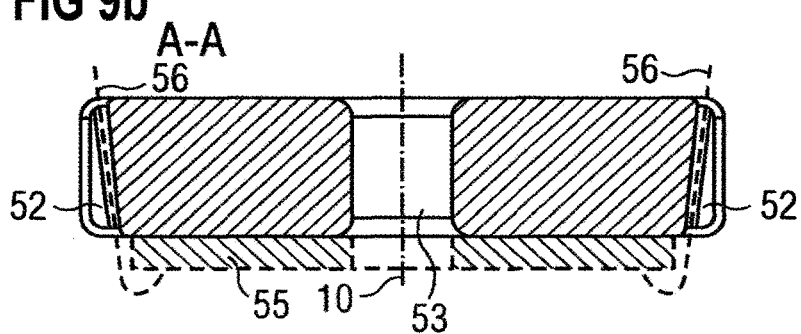

The back plate 50 is illustrated in more detail in different views in FIG. 9 (top view in FIG. 9a, cross-sectional view along line A-A in FIG. 9b, and cross-sectional view along line B-B in FIG. 9c). The back plate 50 has apertures 51 for receiving the reduced-diameter end portions 44 of the shaft portions 41 of the posts 40. Preferably, the number of apertures 51 in the back plate 50 corresponds to the number of posts 40 of the drive unit 4. In the embodiment shown, six apertures 51 are disposed at a regular distance of 60° about the axis of rotation 10, with each of the apertures 51 being at the same distance from the axis of rotation 10. The apertures 51 are shown as extending completely through the back plate 50 in the cross-sectional view of FIG. 9c. However, the apertures 51 may alternatively extend into the back plate 50 only up to a certain depth rather than completely through the back plate 50. A central opening 53 is formed for receiving the bearing pin 15, as described above. The back plate 50 is made of a magnetic material, preferably cobalt steel, to close the magnetic flux path. The diameter of the back plate 50 may be about 5 to 7 mm. Furthermore, notches 52 are provided at the periphery of the back plate 50 for receiving wires 56 to connect the coil windings 47 to a control unit 55, such as a printed circuit board (PCB) at the back of the back plate 50, as shown schematically by dashed lines in FIG. 9b.

Figure 10A:
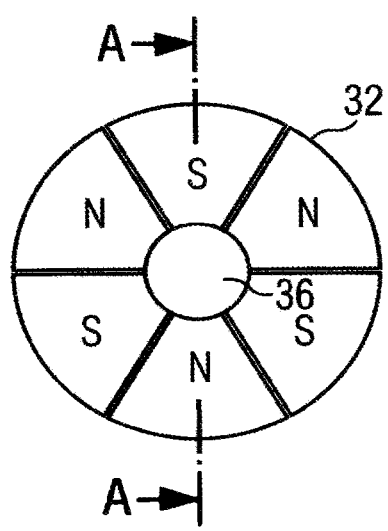
FIGS. 10a-10c show different views of the magnets of the impeller, where
Figure 10B:
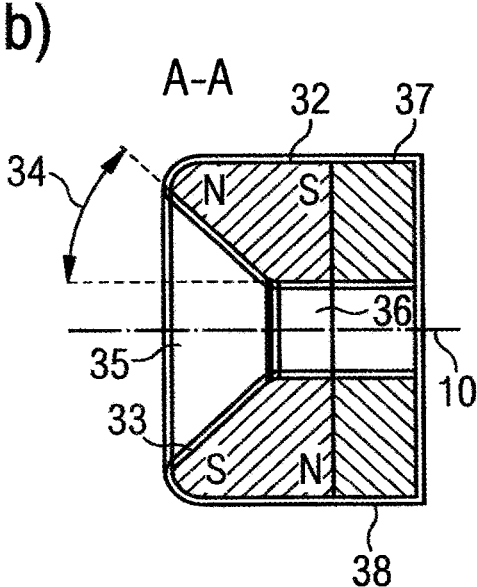
Figure 10C:
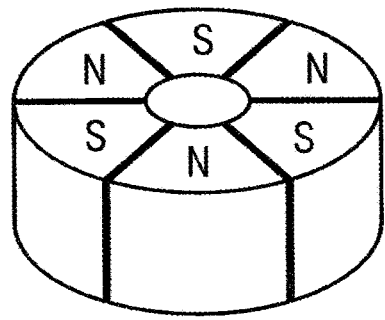

Referring to FIG. 10, the magnet 32 of the impeller 3 (see FIG. 2) is shown in a top view (FIG. 10a), a cross-sectional view (FIG. 10b) and a perspective view (FIG. 10c). In this embodiment, six magnets 32 are provided that are arranged uniformly about the axis of rotation 10, with the orientation of the respective magnetic field alternating. Fewer or more magnets, such as four, eight, ten or twelve magnets, may be provided. The magnets 32 form a recess 35 having a surface 33. The recess 35 corresponds in size and shape to the conical surface formed by the surfaces 43 of the head portions 42 of the posts 40, as shown best in FIG. 6, taking into account the housing 60 that surrounds the drive unit 4, in particular the conical end portion 61 (FIG. 8). It will be appreciated that this includes that the distance between the impeller 3 and the drive unit 4 may not be constant but may increase towards the axis of rotation 10 as explained above. The recess 35 in this embodiment has a conical shape with an angle 34 of 45° with respect to the axis of rotation 10 or longitudinal axis. Other angles, such as 60°, are possible, depending on the shape of the drive unit 4, in particular the end surface formed by the head portions 42 of the posts 40. Furthermore, the magnets 32 form a central opening 36 for receiving the bearing pin 15, as shown in FIG. 2. The central opening 36 is aligned to the central opening 54 of the drive unit 4. As shown in FIG. 10b, the magnetic flux of the magnets 32 is closed by the yoke 37. The yoke 37 may have any suitable shape depending on the shape of the impeller 3, such as conical as shown in FIG. 2 or disc-shaped as indicated in FIG. 10b. Optionally, an encapsulation 38 is provided that encloses the magnets 32 and, if applicable, the yoke 37 to protect the magnets 32 and yoke 37 against corrosion.

Figure 11:
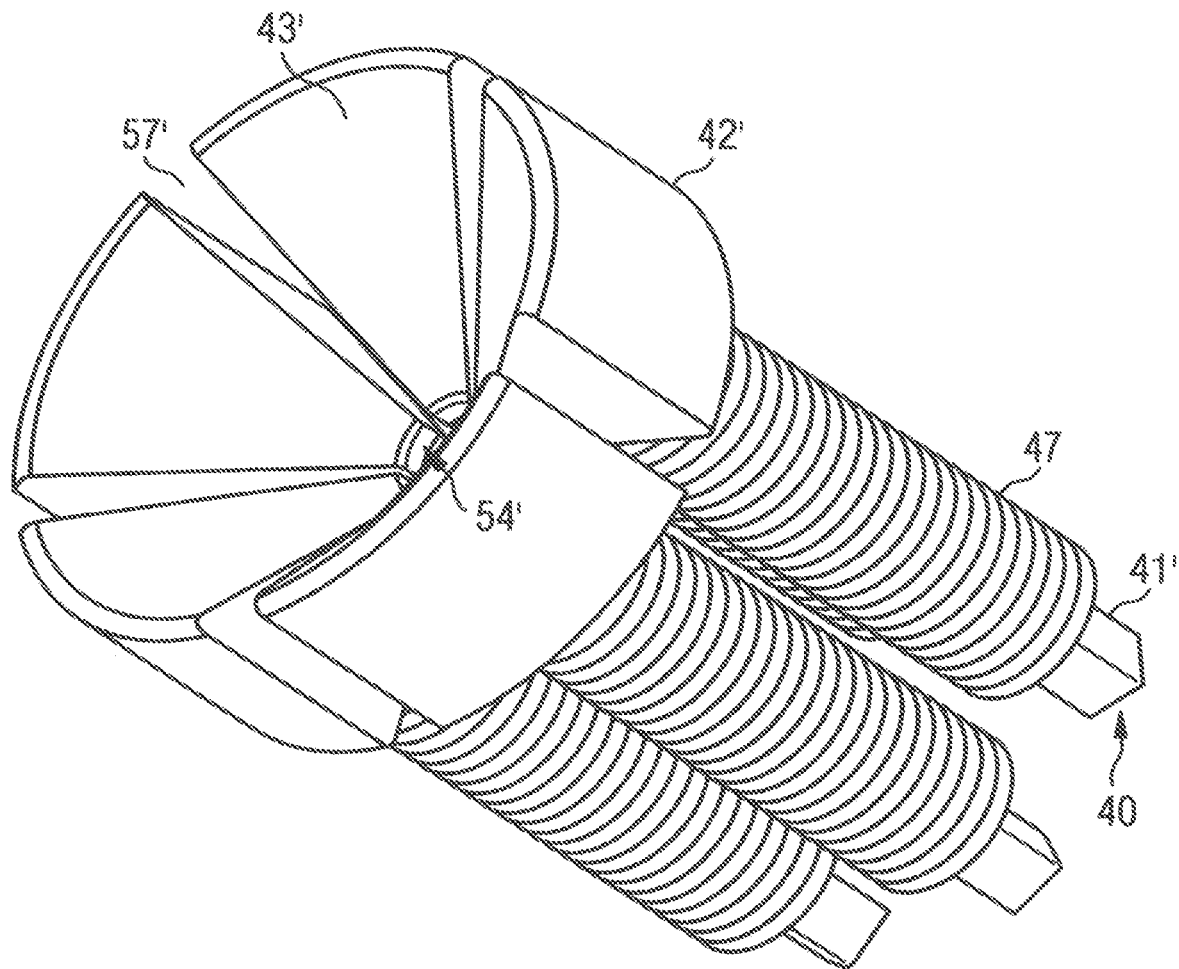
FIG. 11 shows another embodiment of a drive unit.

In FIG. 11 is illustrated another embodiment of a drive unit which is substantially similar to the aforementioned embodiments. The arrangement includes six posts 40' having a respective coil winding 47 on their shaft portions 41'. As in the previous embodiments, there may be fewer or more posts 40'. The posts 40' are preferably attached to a back plate (not shown) as in the previous embodiments. The posts 40 each include a head portion 42', which has a different shape from the above-described head portions 42. Although the angle may be the same as described above, the inclined surfaces 43' face radially inwards rather than radially outwards. That is to say, the head portions 42' form a substantially conical recess. It will be appreciated that the magnet of the impeller will be shaped accordingly, i.e., the magnet will have a corresponding conical shape rather than a conical recess as in the previous embodiments. As in the previous embodiments, the drive unit has a central opening 54'. The posts 40' in the embodiment of FIG. 11 are separated by gaps 57' that prevent a bypass or short-circuit between the posts 40', whereas the head portions 42 of the posts 40 in the previous embodiments are shown to be directly adjacent to each other or separated only by small gaps. It will be appreciated, however, that a short-circuit between the posts is to be avoided in all embodiments.

With reference to FIG. 12, another embodiment of a blood pump 1 is shown, which is similar to that of FIGS. 1 and 2. In contrast to the above embodiment, the blood pump 1 of FIG. 12 has an additional radial hydrodynamic bearing. A circumferential portion 28 of the pump casing 2 or sleeve is provided to form a gap 27 between the impeller 3 and the circumferential portion 28. In addition to the blood flow outlet 22 a further blood flow outlet 29 allows blood to flow through the gap 27 and out of the pump casing 2. The size of the gap 27 is chosen so as to form a radial hydrodynamic bearing.

Figure 13A:
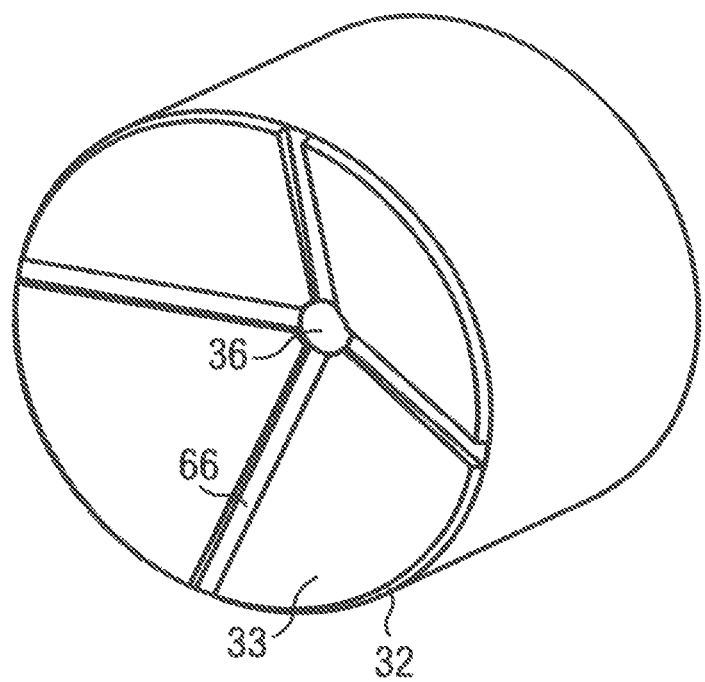
FIGS. 13a and 13b show different views of a drive unit and impeller magnets according to another embodiment.
Figure 13B:
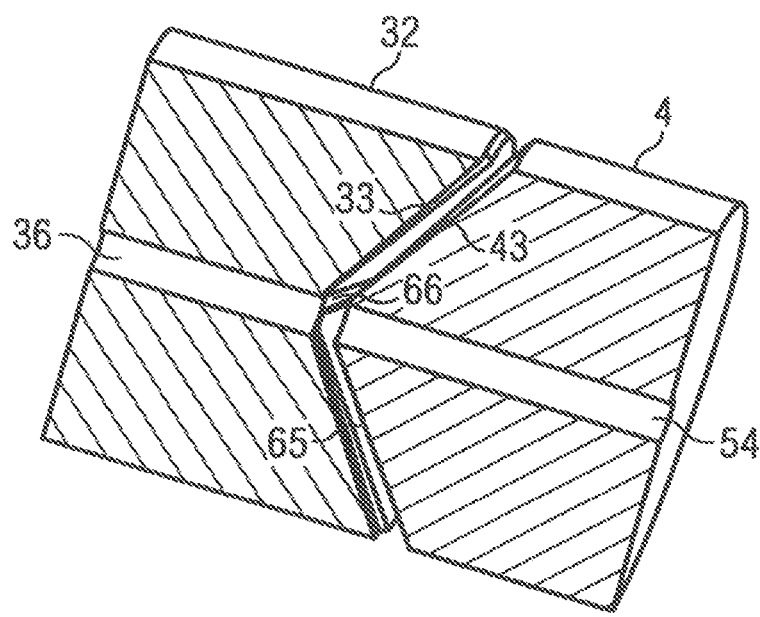

FIGS. 13a and 13b schematically illustrate the magnets 32 of the impeller and the magnets 32 arranged with respect to the drive unit 4. In this embodiment, four magnets 32 are provided that are separated by respective gaps 66. The gaps 66, which may be formed as channels between the surfaces 33 of the magnets 32, extend in a radial direction from the central opening 36 towards the outer perimeter of the magnets 32. As will be described in more detail below with reference to FIGS. 15a and 15b, the reduction of the size of the magnets 32 does not cause a loss of efficiency of the magnetic coupling. FIG. 13b illustrates the relative arrangement of the magnets 32 and the drive unit 4, where a gap 65 is provided between the drive unit 4 (i.e., the stator) and the magnets 32 of the impeller (i.e., the rotor). The channels or gaps 66 improve washing of the gap 65 since they cause a centrifugal pump effect for the blood.

Figure 14A:
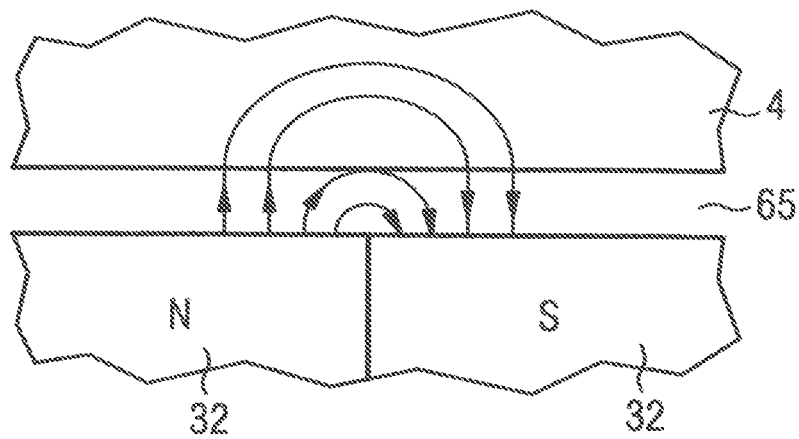
FIGS. 14a and 14b schematically illustrate magnetic field lines between magnets of the impeller.
Figure 14B:
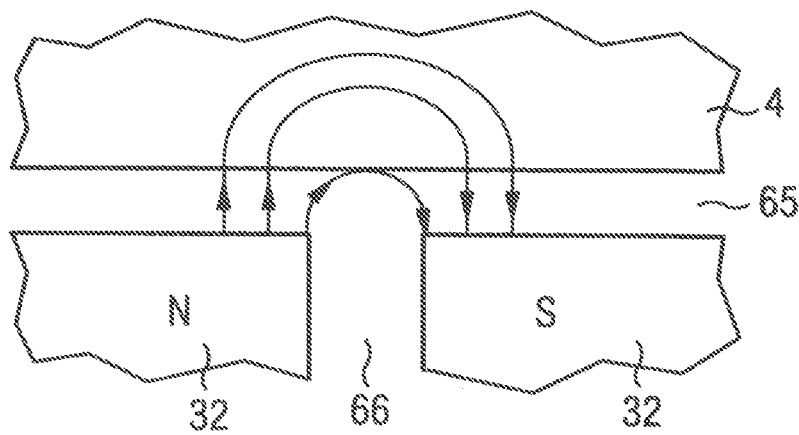
Figure 16:
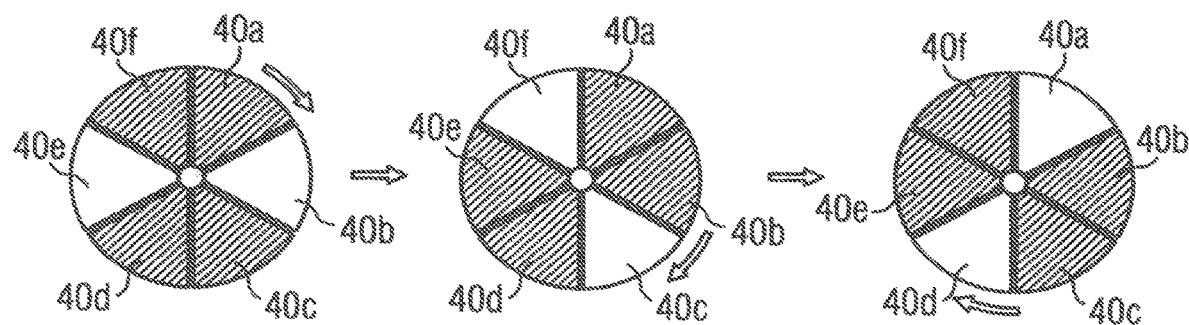
FIG. 16 schematically illustrates an operating mode of the drive unit.

With reference to FIGS. 14a and 14b, the principle of the magnetic coupling between the rotor, in particular the magnets 32, and the stator, i.e., the drive unit 4, is schematically illustrated. In FIG. 14a, the magnets 32 are not or substantially not separated by a gap. Some exemplary magnetic field lines from north N to south S are illustrated. Due to the gap 65 between the drive unit 4 and the magnets 32 the innermost magnetic field lines do not interact with the drive unit 4. That is to say, this part of the magnetic field does not contribute to the drive of the impeller. Thus, no efficiency of the magnetic coupling will be lost if a gap 66 is provided between the magnets 32. In FIG. 14b, the same amount of magnetic field lines reaches the drive unit 4 as in FIG. 14a. As a skilled person knowing the orientation of magnetic field lines is able to calculate, the size of the gap 66 is directly dependent on the size of the gap 65.

With reference to FIG. 15, another embodiment of a drive arrangement for a blood pump is shown. The drive unit 4, including the posts 40 with coil windings 47, is substantially the same as described above. Like reference numerals refer to like parts. As in the previous embodiments, the drive unit 4 includes a back plate 50. However, the design of the impeller is different. In FIG. 15 only the magnets 32 and the yoke 37 of the impeller are shown. The impeller has an increased diameter, in particular a larger diameter than the drive unit 4, and an axial extension 39 such that the extension 39 extends circumferentially about the drive unit 4, in particular in the area of the head portions 42 of the posts 40. This arrangement allows for improved magnetic coupling, as will be explained in the following.

As indicated by some exemplary schematic magnetic field lines, the extension 39 causes the magnetic coupling between the magnets 32 and the drive unit 4 to occur not only in the region of the inclined surfaces 43 but also in the region of the outer side surfaces of the head portions 42 of the posts 40. In this region the magnetic field lines extend in a substantially radial direction between the blood pump's rotor and stator and a high torque can be created to drive the impeller. As also illustrated in FIG. 15, as in all other embodiments, the magnetic field lines form a closed loop that extends through the posts 40, including the head portions 42 and the shaft portions 41, through the magnets 32 and through both end plates or yokes 50 and 37.

With reference to FIG. 13, the operating mode of the drive unit is schematically illustrated in an example having six posts 40a, 40b, 40c, 40d, 40e and 40f. In order to create a rotating magnetic field, the posts are controlled sequentially. The posts are controlled in pairs to establish a balanced rotation of the impeller, in which diametrically opposing posts 40a and 40d, 40b and 40e, and 40c and 40f respectively form pairs. The magnetic density can be increased by activating four of the six posts at the same time. FIG. 13 illustrates a sequence with three steps, in which the activated posts are marked. In the first step, the posts 40a, 40c, 40d and 40f are activated, i.e., a current is supplied to the respective coil winding to create a magnetic field. In the second step, the posts 40a, 40b, 40d and 40e are activated, while in the third step, the posts 40b, 40c, 40e and 40f are activated. This sequence is repeated to create the rotating magnetic field.

The invention claimed is:

1. An intravascular blood pump for percutaneous insertion into a patient's blood vessel, comprising:
    a pump casing having a blood flow inlet and a blood flow outlet,
    an impeller arranged in the pump casing, the impeller rotatable about an axis of rotation, and the impeller having blades sized and shaped for conveying blood from the blood flow inlet to the blood flow outlet, and
    a drive unit for rotating the impeller, the drive unit comprising a plurality of posts arranged about the axis of rotation, wherein each of the posts includes a shaft portion and a head portion, with each of the head portions pointing towards the impeller,
    wherein a coil winding is disposed about the shaft portion of each of the posts, each of the coil windings being sequentially controllable to create a rotating magnetic field,
    wherein the impeller comprises at least one magnet arranged to interact with the rotating magnetic field to cause rotation of the impeller,
    wherein the head portion of each post has a top surface inclined at an angle relative to a plane perpendicular to the axis of rotation, and
    wherein the at least one magnet of the impeller has a surface facing the head portions of the posts and being inclined at an angle corresponding to the angle of the inclined surface of at least one of the head portions.

2. The intravascular blood pump of claim 1, wherein a distance between the axis of rotation and a center of each inclined top surface in a radial direction is less than or equal to a distance between the axis of rotation and a center of a cross-sectional area of each shaft portion of the respective post in a radial direction.

3. The intravascular blood pump of claim 1, wherein at least one of the head portions is triangular in cross-section along a plane including the axis of rotation.

4. The intravascular blood pump of claim 1, wherein the inclined surfaces of the head portions form a conical surface.

5. The intravascular blood pump of claim 4, wherein the at least one magnet of the impeller defines a conical recess corresponding in size and shape to the conical surface formed by the head portions of the posts.

6. The intravascular blood pump of claim 1, wherein the impeller comprises at least two magnets.

7. The intravascular blood pump of claim 1, wherein each of the head portions has a larger cross-sectional dimension than the respective shaft portion in a plane perpendicular to the axis of rotation.

8. The intravascular blood pump of claim 7, wherein each coil winding does not extend beyond the head portion of the post about which it is disposed at least in a radial direction.

9. The intravascular blood pump of claim 1, wherein the drive unit further comprises a back plate which engages ends of the shaft portions of the posts opposite the head portions.

10. The intravascular blood pump of claim 9, wherein the back plate comprises a plurality of apertures arranged about the axis of rotation and receiving the ends of the shaft portions.

11. The intravascular blood pump of claim 9, wherein the back plate includes a diameter in a range of 3 millimeters and 9 millimeters.

12. The intravascular blood pump of claim 1, further comprising a housing surrounding the drive unit.

13. The intravascular blood pump of claim 1, wherein the drive unit has a central opening extending along the axis of rotation.

14. The intravascular blood pump of claim 13, wherein the central opening is configured to receive an elongate pin, with an axial end surface of the pin forming a bearing surface for the impeller.

15. The intravascular blood pump of claim 1, wherein the drive unit is disposed inside the pump casing.

16. The intravascular blood pump of claim 1, wherein the angle is between about 30° and 60°.

17. The intravascular blood pump of claim 1, wherein the angle is about 45°.

18. The intravascular blood pump of claim 1, wherein the inclined surfaces face radially outwards.

19. The intravascular blood pump of claim 1, wherein the impeller comprises at least four magnets.

20. The intravascular blood pump of claim 1, wherein the impeller comprises six magnets.

21. The intravascular blood pump of claim 1, wherein the impeller comprises eight magnets.

22. The intravascular blood pump of claim 21, wherein the magnets are separated by radially extending gaps.

23. The intravascular blood pump of claim 1, wherein the drive unit comprises at least four posts.

24. The intravascular blood pump of claim 1, wherein the drive unit comprises six posts.

25. The intravascular blood pump of claim 1, wherein the drive unit comprises eight posts.

26. The intravascular blood pump of claim 1, wherein intravascular blood pump has an outer diameter in a range of 4 millimeters to 10 millimeters.

27. The intravascular blood pump of claim 1, wherein the plurality of posts are arranged about the axis of rotation such that the plurality of posts include a diameter in a range of 3 millimeters and 8 millimeters.

\* \* \* \* \*